(12) United States Patent
Zagorchev et al.

(10) Patent No.: US 8,862,201 B2
(45) Date of Patent: Oct. 14, 2014

(54) MULTI-MODAL IMAGING SYSTEM AND WORKSTATION WITH SUPPORT FOR STRUCTURED HYPOTHESIS TESTING

(75) Inventors: Lyubomir Zagorchev, Lebanon, NH (US); Andrew Buckler, Wenham, MA (US); Eric Jean, Woburn, MA (US)

(73) Assignee: Koninklijke Philips N.V., Eindhoven (NL)

( * ) Notice: Subject to any disclaimer, the term of this patent is extended or adjusted under 35 U.S.C. 154(b) by 927 days.

(21) Appl. No.: 12/195,627

(22) Filed: Aug. 21, 2008

(65) Prior Publication Data

US 2009/0043172 A1 Feb. 12, 2009

Related U.S. Application Data

(63) Continuation of application No. PCT/US2007/069596, filed on May 24, 2007.

(60) Provisional application No. 60/803,755, filed on Jun. 2, 2006.

(51) Int. Cl.
*A61B 5/00* (2006.01)
*G06F 19/00* (2011.01)
*A61B 6/03* (2006.01)
*A61B 6/04* (2006.01)
*A61B 6/00* (2006.01)

(52) U.S. Cl.
CPC .............. *A61B 6/032* (2013.01); *A61B 5/4821* (2013.01); *A61B 6/0421* (2013.01); *A61B 2503/40* (2013.01); *A61B 6/5247* (2013.01); *A61B 6/467* (2013.01); *A61B 6/0442* (2013.01); *G06F 19/321* (2013.01); *A61B 6/508* (2013.01)
USPC ........... 600/407; 600/411; 600/415; 600/427; 600/436; 119/417; 119/452; 119/751

(58) Field of Classification Search
None
See application file for complete search history.

(56) References Cited

U.S. PATENT DOCUMENTS 5,099,792 A * 3/1992 Cannon et al. ............... 119/420
6,458,081 B1 10/2002 Matsui et al.
6,574,304 B1 6/2003 Hsieh et al.
6,585,647 B1 * 7/2003 Winder .......................... 600/437

(Continued)

FOREIGN PATENT DOCUMENTS

WO 2006020896 A2 2/2006

OTHER PUBLICATIONS

Dazai et al. (Multiple Mouse Biological Loading and Monitoring System for MR, Magnetic Resonance in Medicine 52:709-715, 2004).*

(Continued)

*Primary Examiner* — Unsu Jung
*Assistant Examiner* — Shahdeep Mohammed

(57) ABSTRACT

Investigation of in vivo models of disease requires imaging studies involving single subjects in single imaging sessions, serial imaging of individuals or groups of subjects, and integration of data across diverse and heterogeneous experimental methodologies. Each type of experiment is preferably supported by various feature sets that can be rigorously applied to produce quantitative, reproducible results. Current imaging scanners are not equipped with standardized capability that supports an automated and scientifically rigorous workflow suited to hypothesis testing. An imaging system includes a research workstation at which a user can design, execute, study, and report imaging plans. Flexibility that comes along with a modular design of the system allows the user to customize workflow parameters for more robust hypothesis testing.

31 Claims, 7 Drawing Sheets

(56) References Cited

U.S. PATENT DOCUMENTS

| | | | |
|---|---|---|---|
| 6,983,753 B1* | 1/2006 | Lenhard et al. | 128/898 |
| 7,158,692 B2 | 1/2007 | Chalana et al. | |
| 7,170,974 B2* | 1/2007 | Groh et al. | 378/98.8 |
| 7,395,117 B2* | 7/2008 | Mazar et al. | 607/60 |
| 7,603,165 B2* | 10/2009 | Townsend et al. | 600/427 |
| 7,792,343 B2* | 9/2010 | Pekar | 382/128 |
| 7,865,226 B2* | 1/2011 | Chiodo | 600/407 |
| 2003/0092980 A1 | 5/2003 | Nitz | |
| 2003/0220565 A1* | 11/2003 | Mesaros et al. | 600/437 |
| 2004/0071320 A1 | 4/2004 | Pfister | |
| 2005/0113961 A1 | 5/2005 | Sabol et al. | |
| 2006/0030768 A1* | 2/2006 | Ramamurthy et al. | 600/407 |
| 2006/0058606 A1* | 3/2006 | Davis et al. | 600/407 |
| 2006/0291710 A1* | 12/2006 | Wang et al. | 382/131 |
| 2007/0025606 A1 | 2/2007 | Gholap et al. | |
| 2007/0049815 A1* | 3/2007 | Sanjay-Gopal et al. | 600/407 |
| 2007/0113194 A1* | 5/2007 | Bales et al. | 715/769 |
| 2007/0238946 A1* | 10/2007 | Chiodo | 600/407 |
| 2008/0077025 A1* | 3/2008 | Delgado-Herrera et al. | 600/508 |
| 2009/0080600 A1* | 3/2009 | Keller et al. | 378/18 |

OTHER PUBLICATIONS

Milad et al., "Fear extinction in rats: Implications for human brain imaging and anxiety disorders"; Biological Psychology; vol. 73, pp. 61-71, Feb. 13, 2006.*

* cited by examiner

MULTI-MODAL IMAGING SYSTEM AND WORKSTATION WITH SUPPORT FOR STRUCTURED HYPOTHESIS TESTING

CROSS REFERENCE TO RELATED APPLICATIONS

This application is a continuation of PCT application number PCT/US2007/069596 filed May 24, 2007 which claims the benefit of U.S. provisional application No. 60/803,755 filed Jun. 2, 2006, which is incorporated herein by reference.

BACKGROUND OF THE INVENTION

The present application relates to the in-vivo imaging arts. It finds particular application with workflow and software processing in connection with small animal imaging in a research environment, and will be described with particular reference thereto. It is to be appreciated that the present application also finds use in other clinical and research settings, such as research with human subjects.

Presently available imaging scanners are not equipped with standardized equipment and techniques that support automated and scientifically rigorous workflow suited to the testing of medical hypotheses. Pre-clinical imaging helps to bridge the gap between medical treatment ideas that have not yet been proven reliable and application in human treatment. Pre-clinical animal imaging research can be used to define the conditions and end points for clinical trials. Specifically, pre-clinical in-vivo small animal imaging provides the capability to visualize and quantify metabolic activity, cell proliferation, apoptosis, receptor status and immunoreactions, angiogenesis, and hypoxia, among other relevant biological processes. This is done by indirectly measuring gene expression, enzyme activity, receptors and transporters, and regional concentrations of molecules through a variety of means, most commonly using emission imaging techniques with radiolabeled tracers.

This research is characterized by curiosity and/or by hypothesis driven programs often supported by grants to either discover or explore new insights into biological processes. As such, device characteristics such as sensitivity and spatial resolution are at a premium, particularly when viewed against a continual need to visualize smaller and smaller structures and processes. Additionally, the need for quantification of these processes increases as the research moves from describing systems to measuring systems. This work is primarily conducted in academic medical centers. As such, the knowledge of the community advances through literature, conferences, and symposia. Typically, small scale applications are also pursued for promising research findings. Success criteria include the ability to clearly and effectively demonstrate and expand understanding, whether it results in direct commercial activity or not.

A more specific expression of biological research is the systematic discovery and development of biomarkers, drugs, and therapies that will ultimately be translated from animal models to humans should they prove promising during pre-clinical studies. Distinguishing this area from the more varied general biological area is the need to follow standardized, calibrated processes capable of supporting rigorous regulatory filings. As such, this work is typically (though not exclusively) conducted in commercial pharmaceutical companies and/or instrumentation companies as they seek to discover, develop, and ultimately commercialize drugs and therapies for economic return rather than only build the general knowledge into the processes.

Quantification is important for reliable evaluation of the acquired data. Without the information on tracer concentration in physical, absolute units, different tracers cannot be compared with each other in an objective manner in the context of tracer development. Also, the quality of diagnostic information extracted from the acquired images depends crucially on the quantifiability of the data. Especially from small animal imaging, a variety of considerations such as, for example, partial volume effects play an important role and should be corrected in order to obtain meaningful concentration values. These effects may be mitigated with single-imaging mode design and/or corrections, or through using complementary modality data such as (but not limited to) anatomical information from a CT scan, which can be helpful in this context.

Quantification is valuable in the marketplace. Software tools dealing with partial volume and motion correction, and the like are available, and valuable for reliable quantification. Animal imaging plays an important role in the process of tracer development and validation by reducing the amount of time and effort that has to be spent for evaluating tracer properties. With in-vivo imaging, it is possible to perform a serial analysis of the same animal over a period of time and thus study, for example, the bio-distribution of the tracer over a long time span. Without imaging, the same study would involve many animals, which would have to be sacrificed at various time points to measure the tracer distribution with in-vitro methods. Moreover, by applying such techniques as pharmacokinetic modeling, it is possible to assess multiple biological parameters at once in one imaging procedure.

Pharmacokinetic modeling of pharmacodynamics allows the simultaneous assessment of multiple biological and molecular parameters at once. Since the distribution of the tracer in the animal over the course of time is a dynamic process, static imaging only contains limited information compared to the analysis of dynamic sequences, which provides access to the rate constants governing the kinetic processes.

Pre-clinical applications to support this activity can be summarized as providing users the capability to perform studies of varying scope, each level highlighting requirements or focus areas for the device;

A snapshot measurement on a single subject, e.g., uptake;

Time activity during 1-5 half lives of the radio labeled marker;

A longitudinal study of a single subject across multiple imaging sessions;

A group study with multiple subjects in the same laboratory; and

Population analysis across multiple distributed studies and/or methodologies.

The levels apply most directly to the discovery and development processes for drugs and biomarkers. Software applications implementing these study types is important because doing so facilitates standardization leading to higher quality, more reproducible studies that replace time consuming and error prone manual methods or custom programming that is particularly difficult given the data volume associated with this work. Important standardization should be driven by the instrumentation rather than relying on individual principal investigators.

The present application provides a new and improved small animal handling, imaging, and research data analysis technique that overcomes the above-referenced problems and others.

SUMMARY OF THE INVENTION

In accordance with one aspect, an in-vivo imaging system is provided. At least one imaging modality for acquiring in-vivo imaging data of a subject in an imaging region of the imaging device. A reconstruction processor reconstructs raw data into an image representation. A preparation module provides space where subjects are prepared for imaging in the imaging modality. A research workstation provides a user with an electronic interface to the imaging modality.

In accordance with another aspect, a method of in-vivo imaging is provided. A study is designed for execution on an in-vivo imaging system. Desired data mining and computational bioinformatics activities are selected complement the imaging study. Imaging data is acquired and processed. The processed imaging data is quantified. A statistical analysis is performed on the processed imaging data and/or with results from the computational activities. Then, the statistical analysis is reported in a form that the user chooses.

In accordance with another aspect, a research workstation for designing an in-vivo imaging study is provided. The workstation includes a study design portal for creating and defining the study. A user can select data pertinent to the study from resources to which the workstation has access at a data mining portal. The user can select available tools from image acquisition, reconstruction, and/or image processing portals. The user can select available tools from a pre-defined set of tools and clinical packages at a quantification portal.

The user can select at least one of a pre-defined post processing analysis and an ad-hoc post processing analysis at a statistical analysis portal. A reporting portal allows a user to customize a data reporting method.

In accordance with another aspect, a method of designing a study is provided. A hypothesis capable of being tested in an in-vivo imaging environment is formulated by a user. A study design workflow routine is initiated on a workstation computer. A relationship between imaging and computational methods is specified. Parameters of the study are specified. When the study is designed, a confidence level in the study design is obtained by requesting construction of a model of likely results of the study.

One advantage lies in improved reproducibility of studies.

Another advantage lies in greater flexibility for a user to design and execute studies.

Another advantage lies in access to existing studies and information databases.

Another advantage lies in the ability to se standardized protocols for imaging studies.

Another advantage lies in the structured post processing of imaging data to maximize the statistical confidence of the results.

Another advantage lies in the ability to utilize the reported results in regulatory filings that establish the efficacy of novel diagnostics and therapeutics.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE INVENTION

Figure 1:
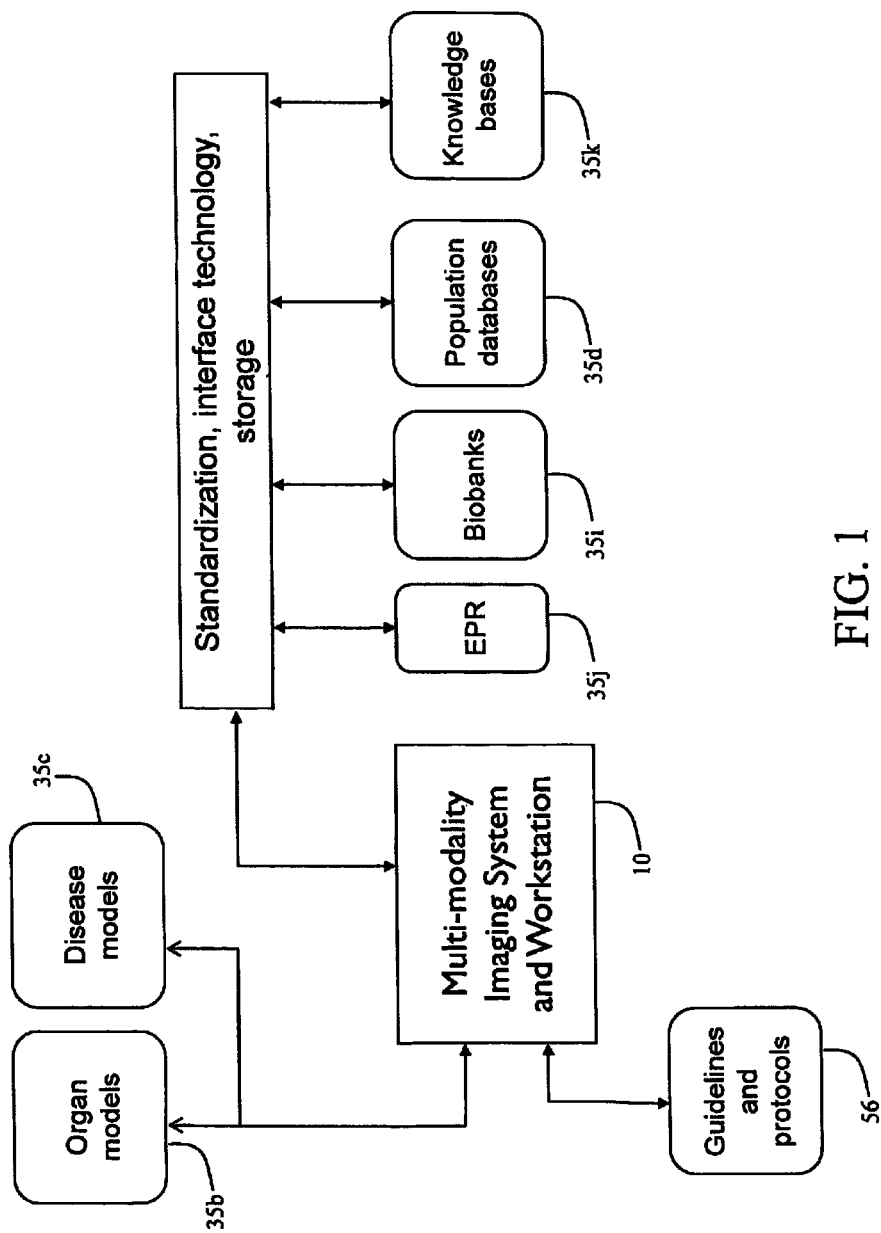
FIG. 1 identifies the context in which the described system and workstation is intended to function.

With reference to FIG. 1, an exemplary context of imaging systems used for diagnostic, therapeutic, and/or research activities is shown.

Figure 2:
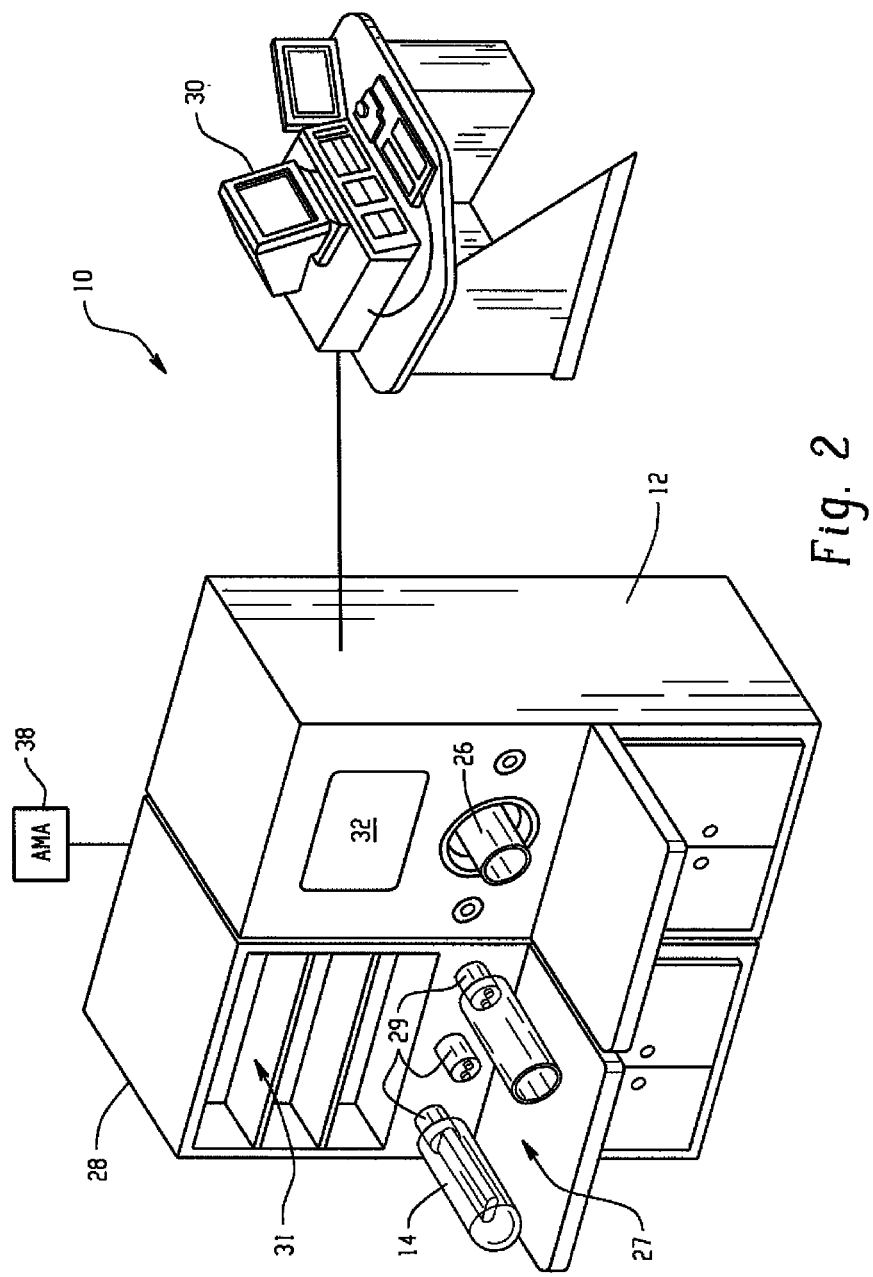
FIG. 2 is a diagrammatic illustration of an animal imaging system, in accordance with the present application.

With reference to FIG. 2 and continuing reference to FIG. 1, an exemplary imaging system 10 is shown. Optional components to facilitate small animal imaging are included on the figure. The present application contemplates a system with modules for positron emission tomography (PET), Computed Tomography (CT), single photon emission computed tomography (SPECT), animal preparation, a research workstation for visualization, image registration, fusion, and analysis capabilities and other imaging and data handling. The various modules are combined within a cover that allows flexible configurations with various combinations of side-by-side, back to back, distributed, and/or in-line configurations, determined by space and throughput issues. A common subject positioner is also contemplated, as well as an animal holder that can be docked and undocked against the positioner. In a side-by side configuration, as shown in FIG. 2, accurate image registration is achieved through the docking feature, which provides positional accuracy and repeatability when the animal holder is docked and undocked. Additional image registration can be obtained through the use of fiducial markers.

Figure 5:
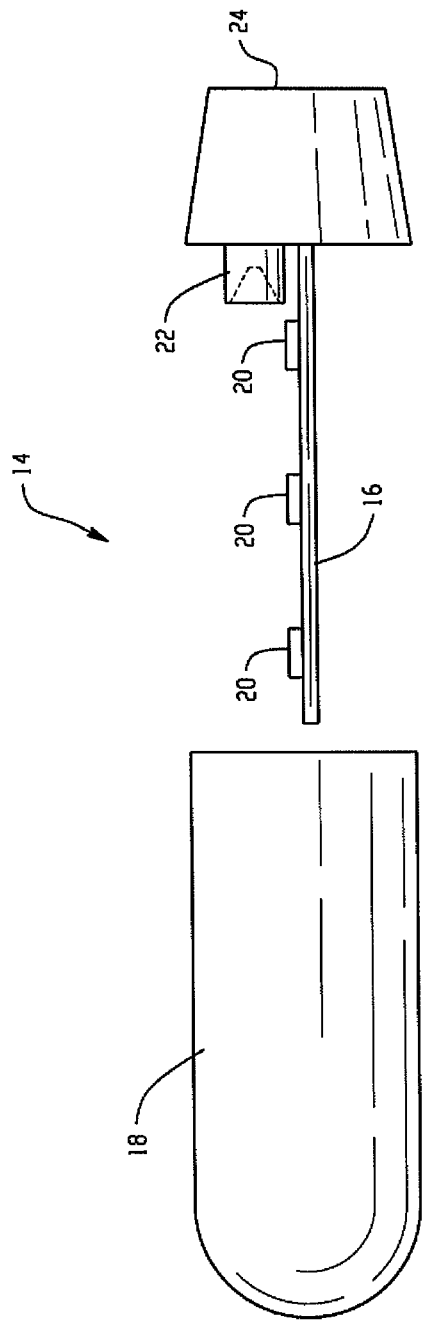
FIG. 5 is a profile view of an animal imaging capsule.

With reference to FIG. 5 and continuing reference to FIG. 2, an imaging modality 12 is responsible for imaging data acquisition. As mentioned above, the modality 12 can be any imaging modality, including but not limited to one or more of PET, SPECT, CT, and MRI. An animal capsule 14 holds one or more animals during imaging sessions. The capsule 14 typically includes one or more holders, or beds 16, a cylindrical cover 18, physiological parameter sensors 20, provisions for anesthesia 22, such as a nose cone into which the animal's nose fits, and a holder-side docking interface 24. Alternately, the cover 18 could include a bag, which can be evacuated to conform to the subject. The docking interface 24 is preferably designed in such way that minimal insert/twist force is applied when the holder is inserted into the imaging modality 12. It is preferable that the position of an animal is not disturbed when it is transferred from one modality to another. By configuring all the modalities and docking stations with a uniform docking interface 24, the handler can exchange the holder between different modalities and docking stations. Docking interface functionality includes providing monitoring, heating and anesthesia interface to the handler, and providing support for up to four animals. For safety reasons, the anesthesia valves can be automatically shut off when the capsule 14 is detached and can be reopened when it is attached. The capsules are preferably constructed to withstand many cleanings and sterilizations, e.g., alcohol, steam, radiation, and the like.

A single animal capsule 14 can support several different bed 16 configurations. One capsule 14 can accommodate up to two (2) rat beds 16, and alternatively, one capsule 14 can accommodate a larger plurality, e.g. four (4), mouse beds 16. Apart from a bed mount, each of the capsule interfaces 24 also provides one or more sockets connected with the measurement sensors 20, a fluid interface for air and anesthesia, and the like. The beds 16 can be either profiled beds or flat pallets. For increasing heating efficiency, it is preferable that separate and as small as possible cylinders 18 be used around each of the animals instead of one large cylinder 18 covering all the animals, although the latter embodiment is by no means unviable. The cylinders 18 are preferably easily removable. Holes are also provided, through which it is possible to insert or pull out catheters for isotope injection and/or optional measurements and physical interactions.

A flat pallet bed type allows animal technicians to work with non-standard measurements or with non-commonly used animals or animal configurations. The technicians can freely place different animals of different sizes and weights. The nosecone 22 on the pallet bed 16 preferably is interchangeable to accommodate different sizes of animals. The nosecone 22 is preferably radio-translucent and tightly covers the animal's head. Additionally, the nosecone 22 can be removed, e.g. if an injected anesthesia is used. The pallet bed 16 is equipped with holes at each side for mounting motion restraints.

In another embodiment, the bed 16 is a form fitting, profiled bed. The profiled bed 16 preferably comes in a few types, each configured to accommodate different animal categories (rats, mice) and sizes (small, medium, large). The bed curves allows for easy and repeatable animal positioning, both with the same subject in temporally remote scans, or with different subjects. Motion restraints are integrated into the bed to prevent re-arrangement of the subject during or between scans. Restraints integrated with the bed 16 are also contemplated in lieu of traditional taping and un-taping.

ECG and respiration probes 20 are preferably integrated with the bed 16. Alternately, sensors can be applied to the subject manually. $SpO_2$ and heating elements may also be parts of the bed 16. Position marks on the bed (i.e. ruler-like markings) assist in reproducing positions when mounting subjects to the bed 16. Given that exact repositioning is desirable in brain imaging, a stereotactic frame may be included. To allow access to the subject without disturbing the subject's position while it is fixed to the bed 16, it is preferable to leave the animal's tail, legs, and eyes accessible while the animal is fixed to the bed 16. It is desirable to autoclave elements that are in contact with animals, so those particular components are preferably resilient to high temperature steam cleaning and disinfection. The beds are independently removable to facilitate access to subjects in multi-animal configurations. With rat and mouse subjects, heated tail holders are preferable because they help prevent tail veins from contracting in a cold environment and altering blood flow rates. Absorbent materials can be included to handle excretion during imaging sessions; the bed design can accommodate disposable materials, or they can be integrated into the bed 16. The bed 16 can be designed with all or most of desired probes embedded into the bed 16. Alternately, the bed can be designed with all probes flexible enough to be placed wherever they are required by the operator. The integrated sensors are useful for standard imaging, specifically where throughput is an issue. External probes can be used in, e.g., complex research scenarios, where it is more important to execute given scenario with maximum accuracy. Although the animal preparation and imaging modules are contemplated and shown side by side, animal preparation and imaging may be located in separate rooms.

With reference again to FIG. 2, the system 10 also includes a subject positioner 26 capable of receiving and docking the capsule 14. The positioner 26 is used to position the animal capsule 14 optimally in an imaging region of the scanner 12 during an imaging session. The capsule 14 has an identifier to provide a unique holder identity to the system. The identity can be read when the holder is connected to the subject positioner 26, e.g. a bar code that moves past a reader during imaging. Though only two modules are depicted in FIG. 2, it is contemplated that several more modules could be added to the system as desired, and as space allows. For instance, A PET module could be next to a CT module. Or, because imaging times are typically longer in PET imaging, several PET modules can be provided for each CT module to improve throughput. The positioner 26 has the capability of taking a capsule 14 from one module to the next e.g., between scans. The positioner 26 may also include capsule rollers capable of rolling the capsule 14 about its longitudinal axis, for orienting the capsule 14 differently.

Figure 3:
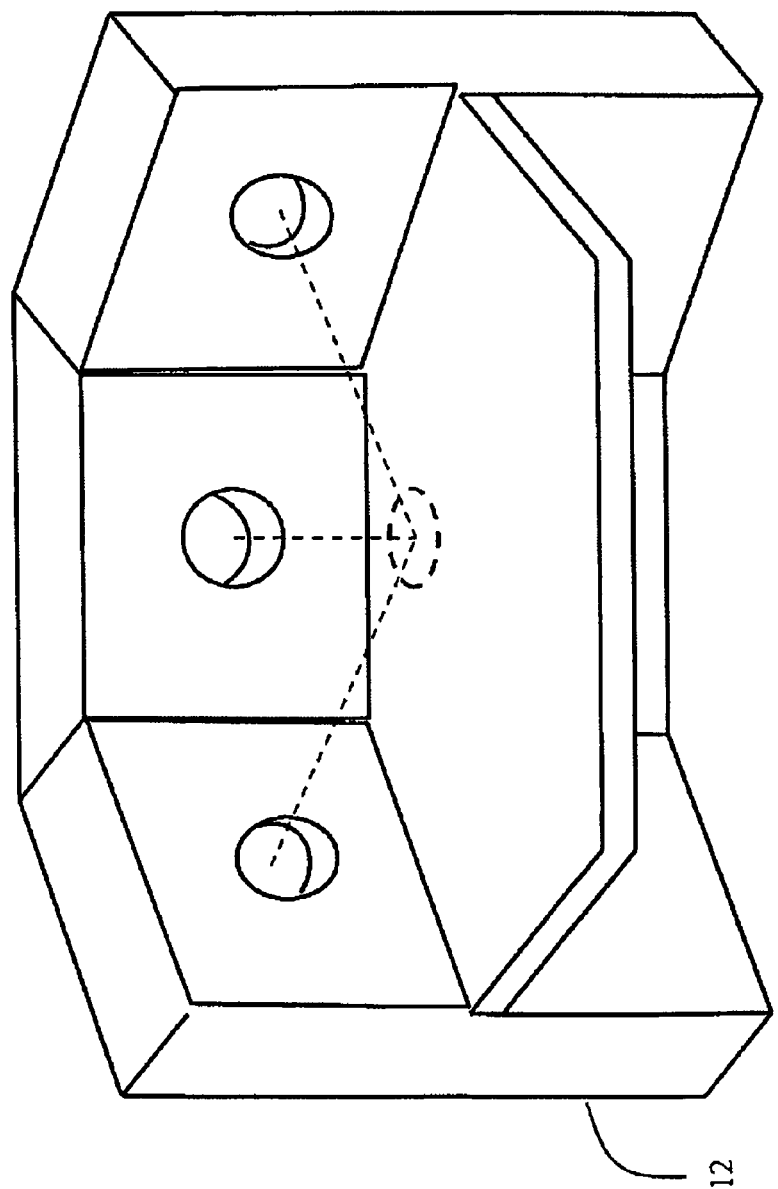
FIG. 3 depicts several modalities oriented radially about a common center point.
Figure 4:
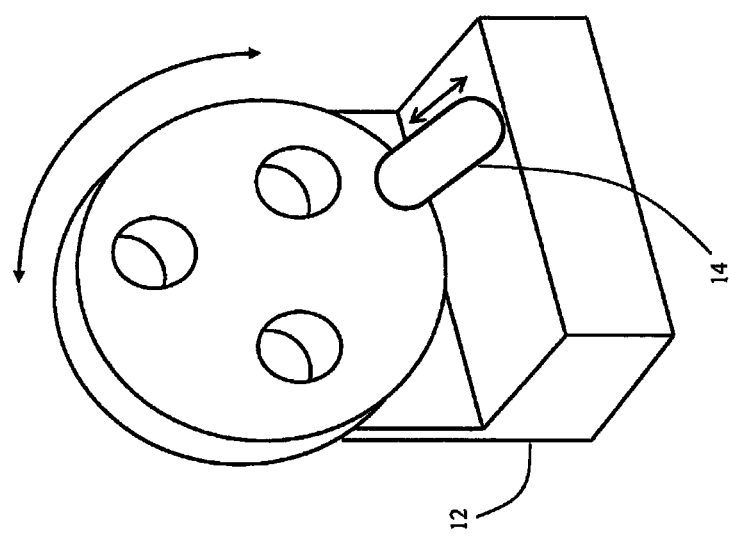
FIG. 4 depicts a rotating gantry with several modalities.

The modules can be arranged side by side in a parallel fashion, as shown in FIG. 2, but, for example, can be oriented serially, that is, one behind another, or radially about a common center point, as depicted in FIG. 3. Another possible orientation of the modalities is a rotating gantry system, as depicted in FIG. 4. It is preferable that the modules 12 are mobile, allowing one to be switched for another, or oriented differently, depending on the user's needs at the time, but permanent or semi-permanent, wall mounted modules have also been contemplated. Mobile modules preferably come equipped with brakes or other anchoring devices to prevent movement after the user has placed the modules in the desired configuration. A docking station 28 provides anesthesia and monitoring while the animal capsule 14 is attached awaiting a scan. As shown, the docking station may include storage space 31 for storage of additional beds 16 cylinders 18 or other devices when not in use. An induction chamber (not shown) provides an area in which a conscious animal is placed so it can be anesthetized before it is mounted on the animal bed 16. Like the modalities 12, it is preferable that the docking station be mobile. This way, the user can move the docking station adjacent to whatever modality 12 with which he or she happens to be working.

In the embodiment of FIG. 2, the system 10 includes two modules, namely the acquisition module 12 and the animal preparation module, that is, the docking station 28. Preferably, the docking station 28 adds several aspects of functionality. These aspects include the induction chamber as previously mentioned, where the subject is brought under anesthesia, a physical workspace 27 to attach the subject to a bed and install the required sensors, docking ports 29 for continuation of life support and anesthesia of the subject between studies, and a "wake up box" that provides life support during wake-up of the subjects (not shown). The preferred method of docking the capsule to the receiving system is through a positive locking mechanism that is engaged through axial force applied by means of an actuator placed in the positioner 26. Again, engagement of the actuator should not require disturbance of the animal. The docking interface 24 on each capsule 14 includes leads to engage an animal monitoring and anesthesia (AMA) system 38, including electrical and gas connections. The anesthesia connection includes an "auto shut-off on disconnection" function to prevent loss of anesthesia to the environment.

Having thus described hardware and modularity of the system, the application now turns to a typical workflow process of imaging a small animal subject. First, the animal is brought to the facility. In the past, animals involved in a study would typically need to be sacrificed in order to acquire ex vivo measurements, essentially freezing uptake characteristics at a point in time. In the present system, such sacrifices are not necessary, so the same animals can be imaged many times over the course of the study. Thus, animals are typically kept on-site, but it is contemplated that they can be brought in from off site. The animal is brought to the scan room and anesthetized. As mentioned previously, this is done with coarse anesthesia in the induction chamber. Once the animal is anesthetized, the animal is positioned and affixed to the imaging bed 16. In addition to positioning the region of interest of the animal, positioning the animal also includes positioning the animals head securely in the nosecone 22 for the automatic, continual delivery of anesthesia. At this time the sensors 20 are attached to the subject animal. Once the animal is positioned on the bed 16 the cover 18 is placed over the animal and the capsule 14 is attached to one of the docking ports 29.

Next, the user calibrates 40 the system. This involves both a software calibration and a hardware calibration, such as X and Y axis zeroing. Once the scanner is calibrated, the positioner 26 relocates the capsule 14 from the docking port 29 on the preparation module 28 to the docking port 29 on the scanning module 12. Once the capsule has been properly positioned in the scanning module, the scan is initiated. While the scan is proceeding, the AMA 38 monitors environmental factors of the capsule 14 and vital signs of the subject, and continuously supplies anesthesia to the subject. Subject monitoring allows the user to eliminate physiological variables to the greatest extent possible. By controlling the physiological variables, study design confidence is enhanced as results will be more readily reproducible. Put another way, fluctuations in physiological variables can taint an otherwise sound study, so it is desirable to control these variables as much as possible.

Once the scan is completed, the animal is removed from the capsule and placed in the post-anesthesia chamber to wake up. Here the AMA 38 monitors the temperature of the chamber. When the animal regains consciousness, it is transferred back to its living environment. The imaging scan can then be processed and integrated into the user's overall clinical study.

To facilitate creation of a study, the system includes a research workstation 30. The workstation 30 includes a computer that controls main system functions and provides an interface for a user to work with the image data. The research workstation 30 includes acquisition control to allow starting, pausing, resuming and stopping an image acquisition and showing status and progress info on the acquisition. The research workstation 30 also interfaces with the AMA 38 in order to display vital signs for multiple animals scanned across several modalities and stages of animal preparation on the workstation. Additionally, acquisition control and a reconstruction user interface may reside in whole or in part on the research workstation 30. Multimodality function is included on the research workstation 30 such as PET-CT non-rigid registration. In such a situation, interfacing with a CT Acquisition control can to be done via the research workstation 30. It is preferable that the research workstation 30 provides a migration path for all applications of the system 10 to use a common platform for infrastructure services and operation. Naturally, the research workstation 30 can be upgraded as new preparation techniques, scanning techniques, software, hardware, and the like become available.

Studies conducted for the purpose of research are often hypothesis driven. A technician or clinician may have an idea and run with it. Perhaps results of one study make technicians ask questions they would not have otherwise asked. Other studies may not be researching entirely new ideas, but bolstering the validity of already-existing hypotheses. In either case, it is beneficial for a technician to have the ability to design and modify imaging studies. This includes both developing new aspects of studies and calling upon known methods and techniques to complement new ideas.

Figure 6:
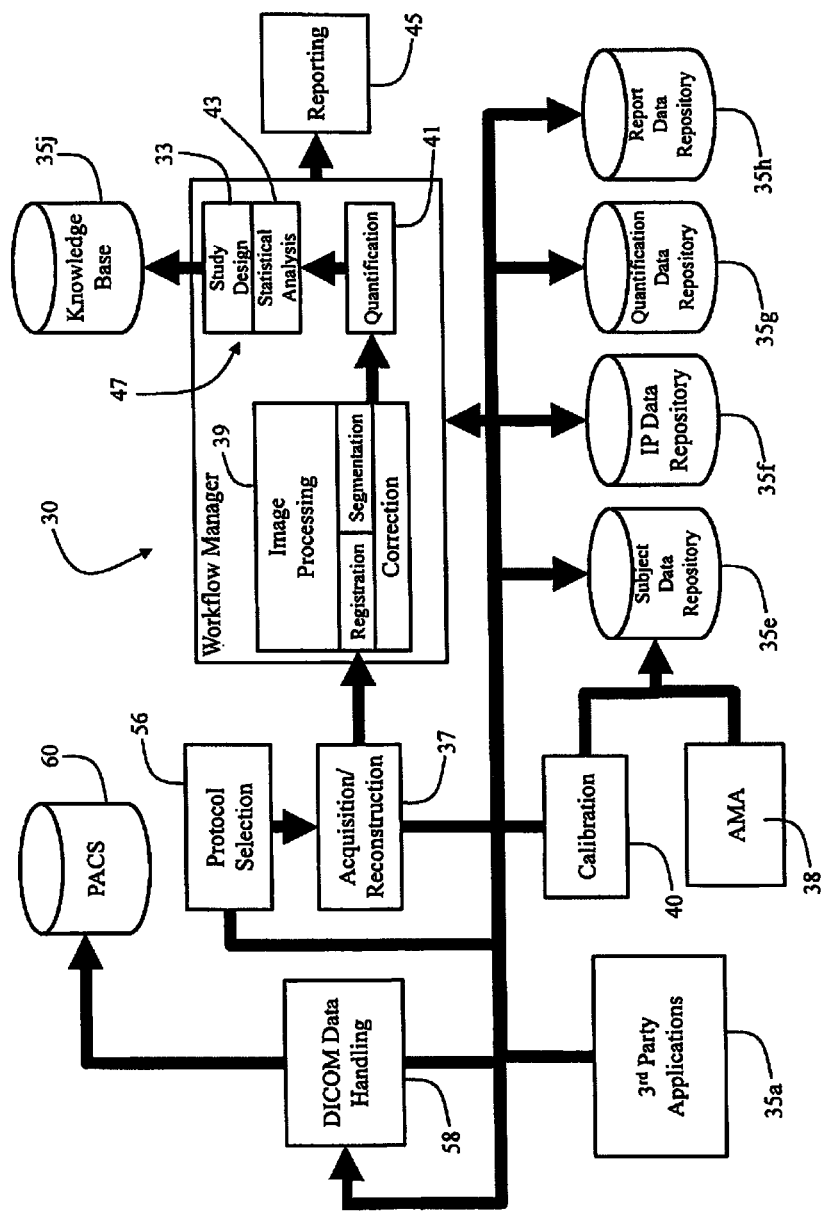
FIG. 6 depicts subsystems of a research workstation available to a user.

With reference to FIG. 6, the research workstation 30 includes functionality for subject and study management. The study management component interacts with a protocol setup component for protocol definition. This allows the user to set up and edit parameters. The research workstation 30 interacts with a modality controller 36 to provide information about active studies and to activate a study. A study is activated on request of the modality controller 36. The research workstation 30 also interacts with the acquisition controller 12, to pass the protocol to the acquisition controller 12 and to start, pause, stop, or resume acquisitions; it receives progress updates from the acquisition controller 12, and can then show them to the user and can pass them to the modality controller 36. Protocol setup in the research workstation 30 preferably allows editing and entry of protocol parameters. The resulting protocol is stored and associated with a study. The research workstation 30 can also receive modification requests from the modality controller 36 and provide protocol info to it. Protocol setup for a study can take place until the moment the study is activated at the modality 12.

Further to study design and management, the research workstation 30 provides a visual user study design interface 33 for assessing study approaches, steps, subject quantities, statistical analysis and other data processing results, and the like. This allows the user to achieve a specified level of confidence given accumulated system accuracies and inaccuracies, as well as specifying a relationship between local imaging and computational methods such as data mining and bioinformatics. The research workstation 30 allows the user to set up complex processes graphically, with the ability to select sequences of steps to conduct a study. The user can designate various widely accepted study types, ranging from loosely structured pilot studies to increasingly rigorous and controlled studies.

The study design capability works by providing a capability for the user to "drag and drop" blocks that represent the various data import, acquisition, processing, quantification, visualization, analysis, and reporting capabilities onto a palette representing the image and data flow according to their needs. The workstation 30 provides a library of blocks that provide a combination of established and novel steps. Once a block is dragged onto the palette, the user is allowed to set "properties" of the block that configure it for the particular study and account for the user defined interconnections that are desired. Calculators to assess system accuracies and confidence levels are provided by the system, along with means to determine a number of subjects or imaging sessions required to achieve a predictive statistical significance with respect to a hypothesis are provided. Results attained from the studies, settings, indexing, data handling, control, and option settings are all associated with the named study and can be recalled for later use. In this manner, a user can simply have the research workstation 30 recall a study that worked well and adapt selected parameters or blocks to create a new study rather than defining a new study from scratch.

The research workstation 30 also includes a data mining/bioinformatics design interface, or portal. This subscreen allows the user to access third party search engines 35a or internal proprietary information applications to access organ models 35b and disease models 35c, population databases 35d, subject specific data 35e, IP data 35f, quantification data 35g, report data 35h, biobanks 35i, the electronic patient chart (EPR) 35j and other knowledge databases 35k. Such information may include editable templates, STL files, normals, collectives, and the like. This aspect provides a place for commercializing informatics research applications that complement standard imaging. Incidentally, after a study has been created and tested, it can be integrated back into the various knowledge databases 35j for future reference.

Another design interface or portal available to the user includes choices concerning image acquisition and reconstruction 37. The research workstation 30 is used to create the study, to register animal data and to invoke a workflow. The research workstation 30 supports the operator workflow in visualizing protocols, providing acquisition control and status and providing images for reviewing. The research workstation 30 has a large, high resolution display connected. This display supports sensitive subject control and provides easy access to large amounts of information. This includes protocol selection and modification. Additionally, the user is able to manage the Digital Imaging and Communications in Medicine (DICOM) 58 format as well as other native imported image formats. Instrument calibration and accuracy data can be transported in private tags. Outside data that does not have instrument calibration and accuracy tags can be hand entered upon a prompt by the research workstation 30. Data can then be output to a picture archiving communication system or PACS 60.

At an image processing workflow design interface 39 the user can select from a variety of post-acquisition image adjustments and enhancements. In one embodiment, this subscreen presents a graphic user interface for registration of various types, surface and volume rendering, model-based segmentation, visualization, fusion, and the like. Additionally the user has the option to select corrections, such as partial volume correction and local motion correction. Data can be represented as a "transform," from multiple inputs to multiple outputs, including displayable portions (e.g. an image) and non-displayable portions (e.g. a deformation field). Also, the image processing subscreen is a convenient place to include longitudinal and group study protocols 56.

The research workstation 30 also includes a quantification design interface 41. At this point, the user can select standard uptake values (SUVs), pharmacokinetics, tools associated with specific organ systems and/or disease processes such as cardiology, neurology, oncology, bone densitometry, neovascularization, as well as other packages. Generally, the user has the option to select existing packages that have been tested and re-used often, as well as packages that are less well known but on their way to becoming accepted packages. It is also preferable that the user have the flexibility to create packages, if desired. Some analysis is generally relevant to the preclinical domain whereas in many cases the packages may be early versions that will ultimately be validated for clinical use. In this way, the system aids translation of capability from animal models to human models.

In a statistical analysis workflow design interface 43, the user can plan and execute analysis of the study that they have previously designed. Here, the user can, for example, utilize Bayesian confidence calculations for hypothesis evaluation 47. Hypothesis evaluation 47 includes both study design 33 and statistical analysis 43. Several automated evaluation frameworks are available in well know study formats, depending on what the user hopes to gain from the data. This subscreen also includes access to statistical calculations for ad-hoc post scan analyses, and is not restricted to pre-designed studies. This way, if the user suspects that there may be some trend or association in the data, they can design their own analyses to investigate it.

Finally, the user has several options when it comes to reporting data. At a reporting design interface 45, charts, graphs, literature summaries, standard FDA reports, and the like are available to the user for reporting their study. Of course, the user can also custom design a reporting method that lends itself to illustrating the instant study. Preferably, the workstation 30 also includes hardware modeling functionality that allows a user to design orientations and arrangements of the hardware the user has at their disposal. As each research setting will have different capabilities and constraints (funding, physical space, etc.) each setting will have different hardware available to it. The user can tell the system what hardware it has available and then design an arrangement to aid in workflow and subject processing. With mobile modular modalities, the user has the flexibility to arrange the modalities to best facilitate execution of his or her hypothesis testing. The system can also take the hardware arrangement into account when evaluating the study, such as identifying potential bottlenecks, problems with keeping the subjects under anesthesia too long, and the like.

Figure 7:
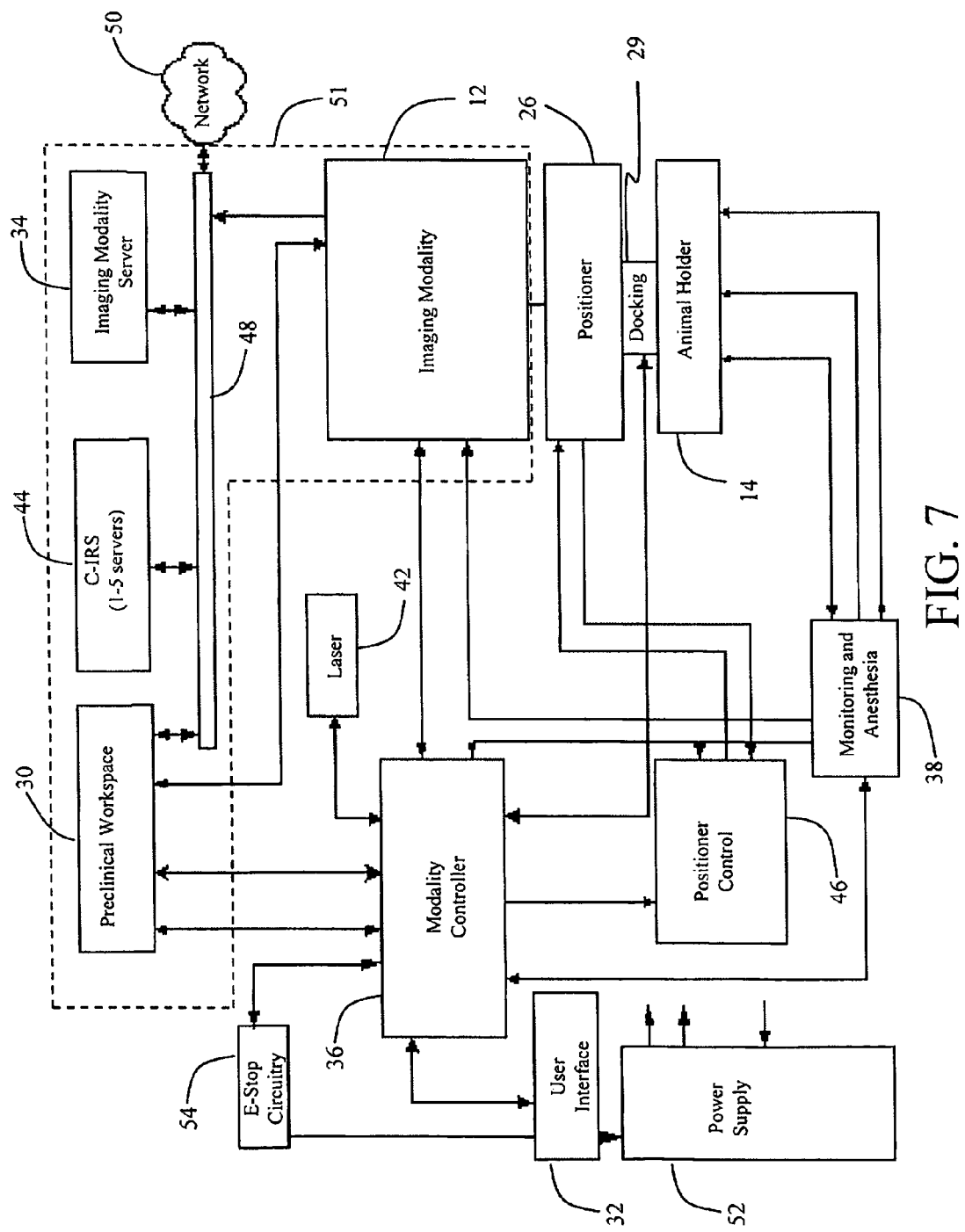
FIG. 7 is a flow diagram that illustrates relationships between components of the system of FIG. 2.

Elements of the system and their relationship to each other are shown in FIG. 7. The imager 12 subsystem includes the detector and the electronics germane to the particular system, whether it be PET, SPECT, CT, MRI, another imaging modality, or a combination thereof. A local user interface 32 provides local user access for instruction entry and status or data read out for the subject positioner 26, the animal monitoring and anesthesia system 38, and imager controls for starting or aborting an acquisition sequence. The local user interface depicted in FIG. 2 is a touch screen, but it could also be a generic detachable control panel that could interface with several different modalities. For modules 12 oriented next to each other, the interface 32 can be mounted on a mobile platform that follows a track along the line of modules, so the interface 32 can be wherever the user happens to be working at the time. In yet another alternate embodiment, the interface 32 could be a wireless device, such as a tablet PC, PDA, or other wireless device that is capable of wireless communication with the system 10.

A server 34 processes data gathered by the scanner 12 and also provides control, reconstruction processing, and support for programmatic interfaces to the acquisition system. The modality controller 36 controls local modality functionalities and keeps track of the studies defined for the modality. These include the AMA subsystem 38, the positioner 26, docking 29, the user interface 32, and a positioning laser 42. The controller 36 also provides input from the interface 32 of the modality 12 to the research workstation computer 30. The controller 36 allows selection of a study when a capsule 14 is attached. It retrieves protocol information for the selected study and allows updating of the selected study. When an acquisition screen at the touch screen 32 is chosen, it activates the study at the research workstation 30, causing the protocol to be loaded into the acquisition controller 12 by the research workstation 30.

The AMA subsystem 38 implements vital signs monitoring (temperature pulse rate, blood pressure, ECG, etc.), anesthesia and waste gas scavenging, and temperature control of the subject or subjects. The AMA subsystem 38 is physically connected to the animal capsule 14 with leads for the monitoring probes 20, a heater for temperature control, and tubes to carry anesthesia and waste gas.

A reconstruction processor 44 is used as a compute resource for reconstruction. The reconstruction processor 44 is connected to the server 34 via a network connection, such as a second thin-net connection that supports raw data handling, reconstruction control, and image transfer handling. Additional modalities can be introduced in the system 10, and in this event, the reconstruction processor 44 can also handle those image formation tasks. In such a case, the reconstruction processor 44 receives raw image data via a proprietary high-speed serial link. The reconstruction processor 44 is connected to the server 34 via a 1 GB thin-net connection, for example, which in turn supports a higher-level programmatic interface for CT reconstruction protocols and image transfer. The server 34 also uses this interface to provide reconstruction control via a programmatic interface to the reconstruction processor unit 44. Preferably, the reconstruction processor 44 includes five servers, but can include more or less as processing tasks demand. The research workstation 30 includes tools as described herein, and suitable rapid prototyping environment software.

A positioner control subsystem 46 interfaces to the modality controller 36, e.g. via an Ethernet connection. Via this connection, movement commands are issued and status and position information is returned. The positioner control 46 is responsible for control of the position of the subject positioner 26. Motion of the positioner 26 is executed through the modality controller 36 and the position controller 46. The modality controller 36 implements the interfaces that perform selected bed motions. The positioner controller 46 translates this into servo commands. A high speed router 48 connects the research workstation 30, the reconstruction processor 44 and the server 34 to the imager 12. The router 48 is preferably a 1 GB intelligent router that allows isolation of the acquisition sub-net(s) from a department or external network 50. The imaging modality 12, research workstation 30, server 34, reconstruction processor 44, and router 48 can be thought of collectively as an acquisition sub-net 51. Logically, the acquisition sub-net 51 links acquisition control (located within the given modality), the server 34, the research workstation 30, and the reconstruction processor 44. This interface carries acquisition control commands from the research workstation 30 to imaging acquisition 12 and the server, allows the research workstation 30 to request subject positioner 26 motion, and provides the path by which raw imaging data is transferred from acquisition 12 to the server 34 and reconstruction processor 44. The intelligent router 48 is used to isolate this logical connection. The connection to the research workstation 30 also supports transfer of minimally processed images to the server platform 34 and to external (i.e. department network) devices 50.

A power supply 52 subsystem provides various AC and DC voltages for the components. Emergency shutoff (E-stop) circuitry 54 cuts electrical power when the circuit is interrupted. When the E-stop circuitry 54 is activated, the power supply will switch to a safe mode, e.g., high voltage and motion control power can be switched off, while computing elements may remain operational. The modality controller 36 is able to read and control the status. It is contemplated that the power system 52 can be factory configurable to accept 120V or 230V AC. Additionally, the power supply will contain a power adaptation module. This module will output 230V in order to supply modules that require higher voltages, such as the reconstruction processor 44.

The Docking Interface module 29 is responsible for allowing accurate docking of the animal capsule 14 to the positioner 26. Furthermore, the module 29 is responsible for making robust electrical and pneumatic connections. The docking interface can be electrically controlled by means of an actuator. Generally, the acquisition module 12 and the docking station 28 are encased in a frame that preferably minimizes the weight and maximizes the rigidity of the system. Additionally, the frame should be virtually transparent to radiation events, so it can encase the bore of the imaging device. Fiberglass is an exemplary frame material. Preferably, a touch screen 32 or other local user interface is included for controlling the positioner 26, displaying AMA data, and to aid in subject positioning. The positioner controller 46 receives motion commands from the touch screen 32 via software also running on the modality controller 36 to perform bed motion. The touch screen 32 provides part of the modality human interfaces. Software for the touch screen 32 runs on the modality controller 36 and interfaces with the AMA 38, motion control and acquisition info components, also running on the modality controller 36. The position of the local user interface 32 is dictated by functional considerations, such as objects typically in or around the bore of the device during imaging, and the like. Preferably, the frame is equipped with cover-switches integrated into the E-stop circuitry to switch of power in case the covers are opened.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An in-vivo imaging system comprising:
   an animal capsule which includes:
     an animal bed configured to receive an animal subject;
     physiological sensors;
     heaters;
     anesthesia cones;
     a single cover which covers the animal bed, the physiological sensors, the heaters, and the anesthesia cones; and
     a mechanical interface;
   a first imaging scanner configured to receive the animal capsule and acquire in-vivo imaging data concurrently of the animal subjects located in the animal capsule and in an imaging region of the first imaging scanner;
   a second imaging scanner that is mobile relative to the first imaging scanner, the second imaging scanner being positionable by a user and configured to receive the animal capsule and acquire in-vivo imaging data of the animal subjects located in the animal capsule concurrently;
   one or more computers programmed to reconstruct the acquired in-vivo imaging data from the first and second imaging scanners into image representations of the animal subject located in the animal capsule;
   a preparation station at which the animal subject is prepared for and recovers from imaging in the first and second imaging scanners, the preparation station and the first and second imaging scanners each having a uniform docking port to which the mechanical interface of the animal capsule is docked during preparation, imaging, and recovery;
   a display on which vital signs of the animal subject in the preparation station and the first and second imaging scanners are displayed;
   a research workstation including:
     an electronic interface which receives the image representations of the animal subject located in the animal capsule,
     a memory which stores at least one study which tests a hypothesis related to the image representations of the animal subject located in the animal capsule, and
   the one or more computers are further programmed to:
     create a new study to test a hypothesis related to the image representation of the animal subject located in the animal capsule, or modify an existing study to test the hypothesis related to image representations of the animal subject located in the animal capsule.

2. The in-vivo imaging system as set forth in claim 1, wherein the one or more computers are further programmed to specify a relationship between imaging and computational methods.

3. The in-vivo imaging system as set forth in claim 1, wherein the one or more computers are further programmed to store indexing settings, data handling settings, control settings, and option settings for later recollection.

4. The in-vivo imaging system as set forth in claim 1, further including:
a touch screen located on one of the imaging scanners through which the user interfaces with the research workstation.

5. The in-vivo imaging system as set forth in claim 4, further including:
a scanner controller that controls local scanner functionalities, keeps track of the studies defined for the scanner, and provides input from the touch screen of the scanner to the research workstation.

6. The in-vivo imaging system as set forth in claim 1, wherein the one or more computers are further programmed to:
calculate a Bayesian confidence measure of the tested hypothesis.

7. The in-vivo imaging system as set forth in claim 1, wherein the one or more computers are further programmed to:
calculate a number of imaging sessions needed to achieve a selected statistical significance with respect to the tested hypothesis.

8. The in-vivo imaging system as set forth in claim 1, wherein the one or more computers are programmed to:
customize a workflow to test the hypothesis;
model modular arrangements to facilitate testing of the hypothesis which includes a measured time each of the animal subjects is under anesthesia;
identify potential problems with an output design; and
suggest an alternative input design.

9. The in-vivo imaging system as set forth in claim 1, wherein the one or more computers are further programmed to:
provide non-rigid registration of image representations of the animal subject located in the animal capsule reconstructed from the acquired in-vivo data with the first imaging scanner and the second imaging scanner.

10. An in-vivo imaging system comprising:
a plurality of animal capsules, each capsule including:
one or more animal beds;
a plurality of physiological sensors,
at least one heater,
a cover which covers the one or more animal beds, the plurality of physiological sensors, and the at least one heater, and
a mechanical interface connected with the plurality of sensors and the at least one heater;
a preparation station which includes a uniform docking port in which the mechanical interface is received and the mechanical interface supplies animal subject data from the plurality of physiological sensors to the uniform docking port when connected to the uniform docking port;
at least one imaging scanner including at least one of positron emission tomography (PET), computed tomography (CT), or a single photon emission computed tomography (SPECT) scanner, which receives at least one animal capsule of the plurality of animal capsules and acquires in-vivo imaging data of animal subjects in an imaging region of the imaging scanner and includes a second uniform docking port in which the mechanical interface is received and the mechanical interface supplies
animal subject data from the plurality of physiological sensors to the second uniform docking port when connected to the second uniform docking port; one or more computers programmed to:
reconstruct the acquired imaging data into image representations of the animal subjects;
receive physiological data while the capsule is docked to the preparation station and the image representations and perform a statistical analysis of the received physiological data and image representations of the animal subjects;
access one or more databases related to the image representations of the animal subjects which store at least one of: organ models, disease models, population data, subject data, quantification data, report data, and biobank data;
create a new study or modify an existing study based on the received image representations of the animal subjects or the statistical analysis of the received physiological data of animal subjects,
mine data from the one or more of the databases in conjunction with the created or modified study.

11. The in-vivo imaging system as set forth in claim 10, further including:
a database that stores at least one of a standardized uptake value tool, a pharmacokinetics tool, a cardiology tool, a neurology tool, an oncology tool, a bone densitometry tool, or a neo-vascularization tool; and wherein the one or more computers are further programmed to:
quantify at least one aspect of the image representations of the animal subjects using bone density tool to measure bone density of the one or more tools retrieved from the database.

12. The in-vivo imaging system as set forth in claim 10, wherein the one or more computers are further programmed to:
customize a workflow to test a hypothesis of the user;
model modular arrangements to facilitate testing of the hypothesis;
identify potential problems and suggest alternatives.

13. An in-vivo imaging system comprising:
a plurality of animal capsules each having a mechanical interface and being configured to receive one or more animal subjects;
at least one imaging scanner having at least one docking port interface configured to receive the animal capsule mechanical interfaces and acquire in-vivo imaging data of the one or more animal subjects contained in one or more of the animal capsules in an imaging region of the scanner;
one or more first computers programmed to reconstruct the acquired in-vivo imaging data of the one or more animal subjects into image representations of the one or more animal subjects;
a preparation station at which the animal subject is prepared for and recovers from imaging in the first and second imaging scanners, the preparation station having a uniform docking port configured to dock the mechanical interface of the animal capsule during preparation;

a research workstation that includes at least one computer programmed to:
  receive the reconstructed image representations of the animal subjects contained in the animal capsule,
  create a new study or modify an existing study which includes the received reconstructed image representations of animal subjects contained in the animal capsule,
  quantify an aspect of the image representations of animal subjects contained in the animal capsule using at least one of a standardized uptake value tool, a pharmacokinetics tool, a cardiology tool, a neurology tool, an oncology tool, a bone densitometry tool, or a neovascularization tool.

14. The in-vivo imaging system as set forth in claim 13, wherein the created or modified study is designed to test a hypothesis and the workstation computer is further programmed to: calculate a confidence value for the hypothesis.

15. The in-vivo imaging system as set forth in claim 13, further including a second imaging scanner arranged in one of a serial, parallel, radial, and rotating relationship with the at least one imaging scanner to facilitate a workflow of the study.

16. The in-vivo imaging system as set forth in claim 13, wherein the workstation computer is further programmed to:
  mine data from previous studies;
  modifying the image representations;
  evaluate and quantify data and the image representation;
  statistically analyze the mined data; and,
  compile a user readable report.

17. An in-vivo imaging system comprising:
  a plurality of animal capsules each having a mechanical interface and configured to receive one or more animal subjects;
  at least one imaging scanner having docking ports configured to dock the animal capsule mechanical interfaces and concurrently acquires in-vivo imaging data of the animal subjects located in the docked animal capsules in an imaging region of the scanner;
  a preparation station at which the animal subjects are prepared for and recovers from imaging in the at least one imaging scanner, the preparation station having at least one uniform docking port configured to dock the mechanical interface of the animal capsule during preparation;
  at least one database that stores knowledge data including at least one of organ models, disease models, subject specific data, and demographic data;
  one ore more computers programmed to:
  reconstruct the acquired in-vivo imaging data of the animal subjects located in the animal capsules into image representations of the animal subjects;
  a user interface on which, to test a hypothesis related to image representations of the animal subjects located in the animal capsules, a user inputs study designs or modifies the study designs related to the image representations of the animal subjects located in the animal capsules, inputs imaging protocols for controlling the at least one imaging scanner, and selects knowledge data to be retrieved from the at least one database;
  a workstation having one or more of the one or more computers programmed to receive the study designs from the user interface, the image representations of the animal subjects located in the animal capsules, the knowledge data and perform a statistical analysis which includes at least one of:
    analyzing the study design;
    calculating a Bayesian confidence evaluation for the hypothesis;
    performing a population analysis over a large subject population; and
    performing an ad-hoc post analysis.

18. The in-vivo imaging system as set forth in claim 17, wherein the one or more computers are further programmed to:
  customize a report to report the statistical analysis.

19. The in-vivo imaging system as set forth in claim 17, wherein each capsule includes:
  a plurality of physiological sensors,
  a heater,
  a first docking interface connected with the sensors and the heater.

20. The in-vivo imaging system as set forth in claim 17, wherein the workstation processor is further programmed to:
  identify potential problems with the selected or modified study design; and suggest alternatives.

21. The in-vivo imaging system as set forth in claim 17, wherein the one or more computers are further programmed to:
  i) initiate a study design workflow routine,
  ii) specify a relationship between imaging and computational methods; and
  iii) specify parameters of the study.

22. An in-vivo imaging system comprising:
  a plurality of animal capsules, each animal capsule including:
    an animal support which supports at least one animal subject,
    a plurality of sensors which measure physiological parameters of the at least one animal subject,
    a heater which controls a temperature of the at least one animal subject;
    a nose cone through which anesthesia is delivered to the at least one animal subject, and
    a mechanical interface connected with the plurality of sensors, the heater, and the nose cone to communicate the measured physiological parameters from the sensors, control signals to the heater, and anesthesia to plurality of nose cones;
  at least one imaging scanner which receives at least one animal capsule of the plurality of animal capsules containing the at least one animal subject and acquires in-vivo imaging data of the at least one animal subject contained in the received one or more animal capsules in an imaging region of the scanner;
  a reconstruction computer programmed to:
    reconstruct the acquired in-vivo imaging data into image representations of the at least one animal subjects contained in the at least one animal capsule;
  a preparation station including a plurality of preparation station mechanical interfaces with which one or more of the animal capsule mechanical interfaces is docked at least one of prior and after the acquiring of the in-vivo imaging data, the preparation station mechanical interfaces receiving the measured physiological parameters from the docked capsule mechanical interface and supplying the heater control signals and the anesthesia to the docked capsule mechanical interface;
  the at least one imaging scanner including an imaging modality mechanical interface to which one or more of the animal capsule mechanical interfaces are docked during the acquiring of the in-vivo imaging data of the at least one animal subject located in the at least one animal capsule, the imaging modality mechanical interfaces receiving the measured physiological parameters of the at least one animal subject located in the at least one animal capsule from the docked capsule mechanical interface and supplying the heater control signals and the anesthesia to the docked capsule mechanical interface; and a workstation including a workstation computer programmed to receive the monitored physiological parameters from the preparation station mechanical interfaces and the imaging modality mechanical interfaces, receive the image representations from the imaging scanner, control the imaging scanner, the capsule heaters, and a supply of anesthesia, and analyze at least the image representation of the at least one animal subject contained in the at least one animal capsule and the monitored physiological parameters.

23. The in-vivo imaging system as set forth in claim 22, wherein the workstation computer is further programmed to:
regulate anesthesia supplied to at least one of the preparation stations and the imaging scanner.

24. The in-vivo imaging system as set forth in claim 22, further including:
a positioner that positions one or more of the animal capsules optimally in an imaging region of the imaging scanner during an imaging session.

25. The in-vivo imaging system as set forth in claim 22, further including:
at least one animal monitor and anesthesia system which monitors vital signs of the animal during a sedation period, and provides regulated anesthesia to the animal via the preparation station and imaging scanner mechanical interfaces.

26. The in-vivo imaging system as set forth in claim 22, further including:
at least one database that stores knowledge data including at least one of subject data, population data, biobank data, and quantification data; and
wherein the workstation computer is further programmed to data mine the at least one database.

27. The in-vivo imaging system as set forth in claim 22, further including:
a database that stores at least one of a standardized uptake value tool, a pharmacokinetics tool, a cardiology tool, a neurology tool, an oncology tool, a bone densitometry tool, and a neo-vascularization tool; and
wherein the workstation computer is further programmed to quantify an aspect of the image representations of the animal subjects contained in the at least one animal capsule using one or more tools retrieved from the database.

28. The in-vivo imaging system as set forth in claim 22, wherein the workstation computer is programmed to perform a statistical analysis and includes at least one of:
evaluate a hypothesis using Bayesian confidence calculations; and
perform a population analysis over a large subject population.

29. The in-vivo imaging system as set forth in claim 22, wherein the workstation computer is further programmed to:
customize a workflow to test a hypothesis;
model modular arrangements to facilitate testing of the hypothesis;
identify potential problems and suggest alternatives.

30. The in-vivo imaging system as set forth in claim 22, wherein the workstation computer is further programmed to:
data mine previous studies;
modify the reconstructed image representations;
evaluate and quantify data and image representations from the studies designed by the study design subsystem;
analyze at least data from the data mining subsystem; and
compile a user readable report.

31. An in-vivo imaging system comprising:
at least one imaging scanner which receives one or more animal capsules in one or more docking ports, acquires in-vivo imaging data of animal subjects contained in the animal capsules in an imaging region of the at least one imaging scanner;
a computer configured to reconstruct the acquired in-vivo imaging data into image representations of the received animal subjects;
a research workstation that includes a computer programmed to:
receive the reconstructed image representation of the animal subjects contained in the animal capsule,
allow a user to input instructions to the computer to create a new pharmacological study or modify a pharmacological existing study to include "drag and drop" blocks that represent the image representations of the animal subjects contained in the animal capsule,
quantify an aspect of the image representations of the animal subjects contained in the animal capsule using a pharmacokinetics tool and at least one of a standardized uptake value tool, a cardiology tool, a neurology tool, an oncology tool, a bone densitometry tool, or a neo-vascularization tool;
a preparation station which includes a second docking port and at which at least one of the animal subjects is prepared for imaging and recovers from imaging in the imaging modality; and
wherein the animal capsule is one of a plurality of animal capsules which hold the animals to be imaged, each animal capsule including a docking interface which is configured to dock in the docking ports in the preparation station and the imaging scanner which provide anesthesia and physiological monitoring at each docked port.

* * * * *